(12) United States Patent
Tamura et al.

(10) Patent No.: US 9,816,918 B2
(45) Date of Patent: Nov. 14, 2017

(54) LASER GAS ANALYZER

(71) Applicant: YOKOGAWA ELECTRIC CORPORATION, Musashino-shi, Tokyo (JP)

(72) Inventors: Kazuto Tamura, Tokyo (JP); Kentaro Hazama, Tokyo (JP); Makoto Kato, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 14/872,759

(22) Filed: Oct. 1, 2015

(65) Prior Publication Data
US 2016/0153896 A1    Jun. 2, 2016

(30) Foreign Application Priority Data

Dec. 1, 2014  (JP) .................................. 2014-243132
Jul. 13, 2015 (JP) .................................. 2015-139847

(51) Int. Cl.
    G01N 21/00    (2006.01)
    G01N 21/31    (2006.01)
    (Continued)

(52) U.S. Cl.
    CPC ........ G01N 21/3103 (2013.01); G01J 3/0202 (2013.01); G01N 15/06 (2013.01);
    (Continued)

(58) Field of Classification Search
    CPC .......... G01J 3/0202; G01J 3/42; G01J 3/0264; G01N 2021/0181; G01N 2021/399;
    (Continued)

(56) References Cited

U.S. PATENT DOCUMENTS 6,538,728 B1    3/2003 Stolle et al.
2007/0242275 A1* 10/2007 Spartz .................. G01N 21/031
                                                            356/451
2014/0226149 A1  8/2014 Coates et al.

FOREIGN PATENT DOCUMENTS

JP    54-21896 A    2/1979
JP    62-87831 A    4/1987
(Continued)

OTHER PUBLICATIONS

Yokogawa Electric Corporation, "General Specifications TDLS200 Laser Gas Analyzer", Mar. 29, 2013 (29 pages total).

*Primary Examiner* — Tri T Ton
(74) *Attorney, Agent, or Firm* — Sughrue Mion, PLLC

(57) ABSTRACT

A laser gas analyzer includes a light emitter which emits a laser light irradiated onto a gas to be measured; a light receiver which receives a laser light which transmitted the gas to be measured; a plurality of optical-axis adjustment mechanisms, one of which is provided in the light emitter and the other one of which is provided in the light receiver; a main display which is provided in one of the light emitter and the light receiver and displays thereon the measured result acquired by receiving the laser light which transmitted the gas to be measured; and a sub-display which is provided in the other one of the light emitter and the light receiver and displays thereon a part of the measured result displayed on the main display.

9 Claims, 7 Drawing Sheets

(51) Int. Cl.
- *G01N 21/61* (2006.01)
- *G01J 3/02* (2006.01)
- *G02B 7/00* (2006.01)
- *G01N 21/01* (2006.01)
- *G01N 21/39* (2006.01)
- *G01N 21/53* (2006.01)
- *G01N 21/85* (2006.01)
- *G01N 15/06* (2006.01)
- G01N 21/3504 (2014.01)
- G01J 3/42 (2006.01)
- G01N 21/59 (2006.01)

(52) U.S. Cl.
CPC ............. *G01N 21/01* (2013.01); *G01N 21/39* (2013.01); *G01N 21/534* (2013.01); *G01N 21/61* (2013.01); *G01N 21/85* (2013.01); *G02B 7/003* (2013.01); *G01J 3/42* (2013.01); *G01N 21/3504* (2013.01); *G01N 21/59* (2013.01); *G01N 2015/0693* (2013.01); *G01N 2021/0181* (2013.01); *G01N 2021/399* (2013.01); *G01N 2021/536* (2013.01); *G01N 2021/8578* (2013.01); *G01N 2201/024* (2013.01); *G01N 2201/06113* (2013.01)

(58) Field of Classification Search
CPC ..... G01N 2021/536; G01N 2021/8578; G01N 21/01; G01N 21/3103; G01N 21/3504; G01N 21/39; G01N 21/534; G01N 21/59; G01N 21/61
USPC ................................................. 356/432–444
See application file for complete search history.

(56) References Cited

FOREIGN PATENT DOCUMENTS

| | | | |
|---|---|---|---|
| JP | 2008-232918 A | | 10/2008 |
| JP | 2010-96631 A | | 4/2010 |
| JP | 2010096631 A | * | 4/2010 |

\* cited by examiner

LASER GAS ANALYZER

BACKGROUND OF THE INVENTION

Field of the Invention

Priorities are claimed on Japanese Patent Application No. 2014-243132, filed Dec. 1, 2014, and Japanese Patent Application No. 2015-139847, filed Jul. 13, 2015, the contents of which are incorporated herein by reference.

Embodiments of the present invention relate to laser gas analyzers.

Related Art

A laser gas analyzer is a device which irradiates a laser light onto a gas to be measured and measures components contained in a gas to be measured and the concentration, etc., thereof based on the absorption spectrum of a laser light which transmits the gas to be measured. This laser gas analyzer is configured to generally include a light emitter which emits a laser light for irradiating onto the gas to be measured and a light receiver which receives a laser light which transmitted the gas to be measured. Such a laser gas analyzer is often installed such that the light emitter and the light receiver face each other with a smoke duct placed therebetween. The smoke duct is a duct through which the gas to be measured is guided.

An optical axis adjustment mechanism which is a mechanism for an optical axis adjustment is provided in the light emitter and the light receiver of the laser gas analyzer, and the optical axis adjustment is performed between the light emitter and the light receiver at the time of periodic or aperiodic maintenance as well as at the time of installation of the laser gas analyzer. This is because, when there is an offset between an optical axis of the light emitter and an optical axis of the light receiver, a light amount of the laser light received in the light receiver decreases to cause the measurement accuracy to decrease.

The optical axis adjustment between the light emitter and the light receiver of the laser gas analyzer is generally performed in accordance with the following procedures:

(1) The optical axis of the light emitter is adjusted such that the transmittance of the laser light is maximal;

(2) The optical axis of the light receiver is adjusted such that the transmittance of the laser light is maximal; and (3) The optical axis of the light emitter is adjusted such that the transmittance of the laser light is maximal.

One example of a laser gas analyzer which makes it possible to adjust an optical axis over a wide range is disclosed in JP2010-096631A.

In a related-art laser gas analyzer, a calculation device which calculates components included in a gas to be measured and the concentration, etc., thereof; and calculated results or measured results of the calculation device. Therefore, the optical axis adjustment of the light emitter of the above-described procedures (1) and (3) can be performed by a worker himself while he checks the display content or the transmittance of the laser light of the display. However, it is difficult to perform the optical axis adjustment of the light receiver that is described above in the procedure (2) by the worker himself because the worker may not visually check the transmittance of the laser light.

Thus, presently, a worker who performs the optical axis adjustment of the light emitter and a worker who performs the optical axis adjustment of the light receiver work as a pair and, when the optical axis adjustment of the light receiver is performed, the optical axis adjustment of the light receiver is performed while conveying the display content of the display using communications devices such a transceiver, a mobile telephone, a PHS or a personal handyphone system, etc. In this way, presently the efficiency is poor due to the fact that at least two workers are needed to perform the optical axis adjustment between the light emitter and the light receiver of the laser gas analyzer.

Moreover, when the diameter of the smoke duct along which the light emitter and the light receiver of the laser gas analyzer reaches several tens of meters, the transmittance of the laser light decreases significantly with a slight offset in the optical axis. In such a case, although it is not impossible to perform the optical axis adjustment of the light receiver with a method of performing the optical axis adjustment while conveying the content of the display using the communications devices, the task efficiency is substantially reduced relative to a method of performing the optical axis adjustment while the worker visually checks the content of the display.

SUMMARY

In light of the circumstances as described above, an object of embodiments of the present invention is to provide a laser gas analyzer which makes it possible for one worker to efficiently perform an optical axis adjustment by himself.

According to an embodiment of the present invention, a laser gas analyzer is provided, including: a light emitter which emits a laser light irradiated onto a gas to be measured; a light receiver which receives a laser light which transmitted the gas to be measured; a plurality of optical-axis adjustment mechanisms, one of which is provided in the light emitter and the other one of which is provided in the light receiver; a main display which is provided in one of the light emitter and the light receiver and displays thereon the measured result acquired by receiving the laser light which transmitted the gas to be measured; and a sub-display which is provided in the other one of the light emitter and the light receiver and displays thereon a part of the measured result displayed on the main display.

Moreover, in the laser gas analyzer according to an embodiment of the present invention, the main display displays thereon at least information which indicates a concentration of the gas to be measured and a transmittance of the laser light, and the sub-display displays information indicating the transmittance of the laser light as a part of the measured result.

Furthermore, the laser gas analyzer according to an embodiment of the present invention further includes a calculation device which is provided in one of the light emitter and the light receiver and which calculates the measured result using a light receiving signal which is acquired by receiving the laser light which transmitted the gas to be measured.

Moreover, in the laser gas analyzer according to an embodiment of the present invention, the main display and the calculation device are provided in the light receiver, and the sub-display is provided in the light emitter.

Furthermore, the laser gas analyzer according to an embodiment of the present invention further includes a memory which stores therein a threshold value for a transmittance of the laser light, wherein the main display and the sub-display displays the measured result and the part of the measured result in modes which are different when the transmittance of the laser light does not exceed the threshold value and when the transmittance of the laser light exceeds the threshold value.

Moreover, the laser gas analyzer according to an embodiment of the present invention further includes an output terminal which externally outputs signals which are different when the transmittance of the laser light does not exceed the threshold value and when the transmittance of the laser light exceeds the threshold value.

Furthermore, in the laser gas analyzer according to an embodiment of the present invention, at least one of the main display and sub-display varies at least a part of the display content for each calculation period of the calculation device.

Moreover, in the laser gas analyzer according to an embodiment of the present invention, a light emitting element which emits light for each calculation period of the calculation device is included in at least one of the light emitter and the light receiver.

According to an embodiment of the present invention, a laser gas analyzer is provided, including a light emitter which emits a laser light irradiated onto a gas to be measured; a light receiver which receives a laser light which transmitted the gas to be measured; a plurality of optical-axis adjustment mechanisms, one of which is provided in the light emitter and the other one of which is provided in the light receiver; a main display which is provided in the light receiver and which displays thereon the measured result acquired by receiving the laser light which transmitted the gas to be measured; a sub-display which is provided in the light emitter and displays thereon a part of the measured result displayed on the main display; a calculation device which is provided in the light receiver and which performs a calculation on the measured result using a light receiving signal which is acquired by receiving the laser light which transmitted the gas to be measured, the calculated measured result including a transmittance of the laser light; and a memory which stores therein a threshold value for the transmittance of the laser light, wherein the calculation device compares the stored threshold value in the memory and the transmittance of the laser light that is acquired using the light receiving signal, determines whether the transmittance of the laser light exceeds the stored threshold value, and causes the measured result to be displayed on the main display in a first mode when the transmittance of the laser light does not exceed the stored threshold value and causes the measured result to be displayed on the main display in a second mode when the transmittance of the laser light exceeds the stored threshold value and the first mode and the second mode are different from each other.

Moreover, in the laser gas analyzer according to an embodiment of the present invention, the calculation device further causes the measured result to be displayed on the sub-display in a third mode when the transmittance of the laser light does not exceed the stored threshold value and causes the measured result to be displayed on the sub-display in a fourth mode when the transmittance of the laser light exceeds the stored threshold value and the third mode and the fourth mode are different from each other.

According to embodiments of the present invention, a main display which displays measurement results obtained by receiving a laser light which transmitted a gas to be measured is provided on one of a light emitter and a light receiver, and a sub-display which displays a part of measured results displayed on the main display is provided on the other one of the light emitter and the light receiver, making it possible for one worker to efficiently perform optical axis adjustment.

DETAILED DESCRIPTION OF THE INVENTION

Figure 1:
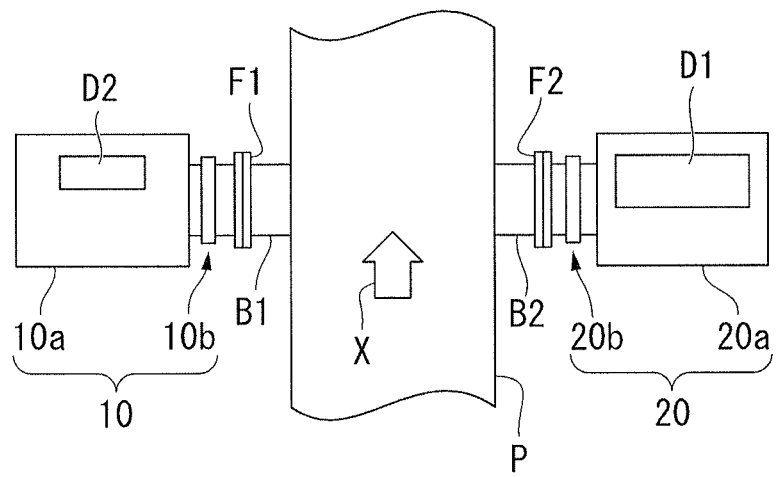
FIG. 1 is a diagram illustrating a schematic configuration of a laser gas analyzer according to one embodiment of the present invention.

A laser gas analyzer according to one embodiment of the present invention is described with reference to the drawings. FIG. 1 is a diagram illustrating a schematic configuration of a laser gas analyzer according to one embodiment of the present invention. As shown in FIG. 1, a laser gas analyzer 1 according to the present embodiment that includes a light emitter 10 and a light receiver 20 that are installed such that they face each other with a smoke duct or a pipe P along which a gas to be measured X is guided being placed therebetween irradiates a laser light on the gas to be measured X that flows the pipe P and measures components included in the gas to be measured X, the concentration thereof, etc., based on the absorption spectrum of the laser light which transmitted the gas to be measured.

The light emitter 10, which is mounted to a fixed flange F1 of a branch pipe B1 which is formed on a side wall of the pipe P, emits a laser light which is irradiated onto the gas to be measured X that flows through the pipe P. The laser light which is emitted from the light emitter 10 is guided to the pipe P via the inside of the branch pipe B1. This light emitter 10 includes a light emitter body 10a and an optical axis adjustment mechanism 10b.

The light emitter body 10a, which accommodates an optical element (not shown) such as a collimating lens, etc., a light emitting element (not shown) such as a semiconductor laser, etc., emits a laser light which is irradiated onto the gas to be measured X that flows through the pipe P. Moreover, a sub-display D2, for which details are described below, is provided in this light emitter body 10a. The optical axis adjustment mechanism 10b is a mechanism for adjusting an optical axis of the light emitter 10.

The light receiver 20 is mounted to a fixed flange F2 of a branch pipe B2 which is formed on a side wall of the pipe P or a branch pipe formed such as to be arranged on the same straight line as the branch pipe B1 receives a laser light which transmitted the gas to be measured X that flows the pipe P to determine the absorption spectrum and measures the components contained in the gas to be measured X and the concentration thereof based on this absorption spectrum. The laser light which transmitted the gas to be measured X is guided to the light receiver 20 via the inside of the branch pipe B2. This light receiver 20 includes a light receiver body 20a and an optical axis adjustment mechanism 20b.

The light receiver body 20a, which accommodates an optical element (not shown) such as a condensing lens, etc., a light receiving element (not shown) such as a photodiode, etc., receives the laser light which transmitted the gas to be measured X and measures the components contained in the gas to be measured X and the concentration thereof, etc. The optical axis adjustment mechanism 20b is a mechanism for adjusting an optical axis of the light receiver 20.

Figure 2:
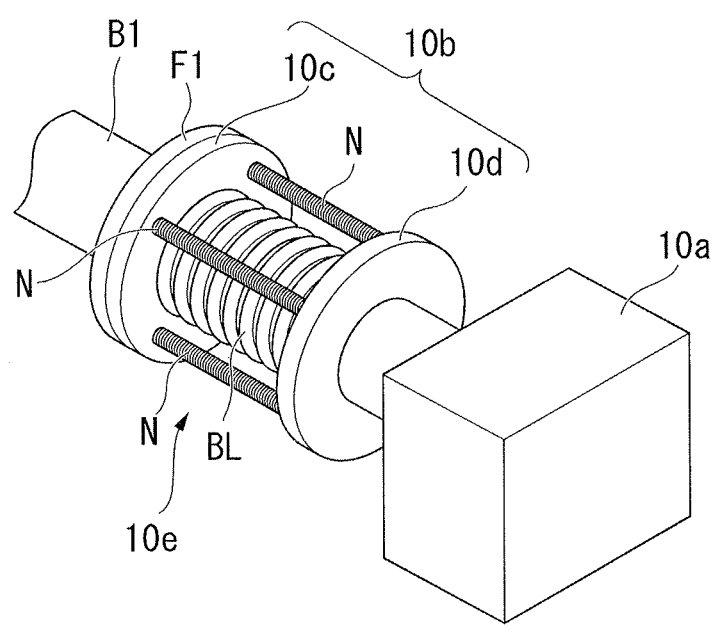
FIG. 2 is a perspective diagram illustrating an optical axis adjustment mechanism which is provided in the laser gas analyzer according to one embodiment of the present invention.

FIG. 2 is a perspective diagram illustrating an optical-axis adjustment mechanism which is provided in the laser gas analyzer according to one embodiment of the present invention. The optical axis adjustment mechanism 10b, which is provided in the light emitter 10, and the optical axis adjustment mechanism 20b, which is provided in the light receiver 20, represents the same mechanism, so that the optical axis adjustment mechanism 10b, which is provided in the light emitter 10, is explained. As shown in FIG. 2, the optical axis adjustment mechanism 10b includes a mounting flange 10c, a mounting flange 10d, and an adjuster 10e. The mounting flange 10c is a flange for mounting the optical axis adjustment mechanism 10b onto a fixed flange F1, while the mounting flange 10d is a flange for mounting the light emitter body 10a onto the optical axis adjustment mechanism 10b. The adjuster 10e includes a bellows BL and four adjusting screws N.

The bellows BL, which is a flexible cylindrical tube, is provided such that it covers the periphery of an optical route or an optical route of the laser light between the mounting flange 10c and the mounting flange 10d. More specifically, the bellows BL is mounted onto the mounting flange 10c such that one end thereof surrounds over the whole periphery of a hole (not shown) which is formed at a central portion of the mounting flange 10c, while the other end thereof surrounds over the whole periphery of a hole (not shown) which is formed at a central portion of the mounting flange 10d.

The adjusting screws N, which are screws for coupling the mounting flange 10c and the mounting flange 10d and adjusting an optical axis of the light emitter 10 and is provided in equal intervals along the peripheral direction on the external periphery side of the bellows BL. One or multiple rotation amounts of these four adjusting screws N may be adjusted to arbitrarily adjust the slope of the light emitter body 10a or the slope relative to a face which is parallel to the fixed flange F1.

Figure 3:
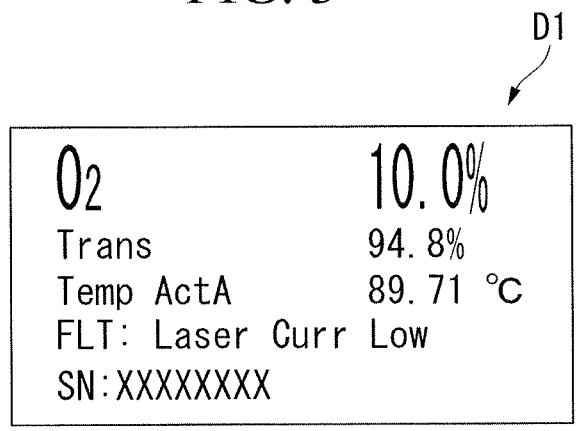
FIG. 3 is a diagram illustrating one example of the display content of a main display which is provided in the laser gas analyzer according to one embodiment of the present invention.

FIG. 3 is a diagram illustrating one example of the display content of a main display which is provided in the laser gas analyzer according to one embodiment of the present invention. The main display D1 provided in the light receiver body 20a of the light receiver 20, which is a liquid crystal display or an LCD, for example, displays multiple measured results or the concentration of the gas to be measured X and the transmittance of the laser light which are acquired by receiving the laser light which transmitted the gas to be measured X.

In the example shown in FIG. 3, "10.0%" is displayed as the concentration "$O_2$" of the gas to be measured X, "94.8%" is displayed as the transmittance "Trans" of the laser light, and "89.71° C." is displayed as the temperature "TempActA" of the gas to be measured X. Moreover, a display of "Laser Curr Low", or a display which indicates that current supplied to the light emitting element of the semiconductor laser, etc., is small as an alarm "FLT" and "XXXXXXXX" as a serial number "SN" of the laser gas analyzer 1 are displayed. In addition to these, information indicating measurement conditions or, for example, a measurement range may be displayed. Moreover, with respect to the display of the alarm, a separate lamp may be provided in the periphery of the main display D1 and an alarm generation may be displayed by turning on a lamp.

Figure 4:
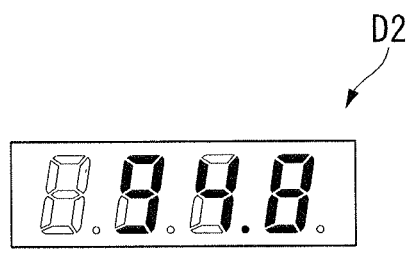
FIG. 4 is a diagram illustrating one example of the display content of a sub-display which is provided in the laser gas analyzer according to one embodiment of the present invention.

FIG. 4 is a diagram illustrating one example of the display content of a sub-display which is provided in the laser gas analyzer according to one embodiment of the present invention. A sub-display D2 which is provided in the light emitter main body 10a of the light emitter 10, which is a 7-segment LED or light emitting diode, for example, displays a part of measured results displayed on the main display D1. In an example shown in FIG. 4, the transmittance "94.8" of the laser light that is displayed on the main display D1 is displayed.

The main display D1 shown in FIG. 3 needs to display multiple measured results, the alarm, etc., that are acquired by receiving the laser light which transmitted the gas to be measured X, so that a display such as a liquid crystal display, etc., is used. On the other hand, the sub-display D2 is basically used only at the time of optical axis adjustment of the light emitter 10, and it suffices that a part of the display content of the main display D1 or the transmittance of the laser light in the example shown in FIG. 4 be displayed, so that a display such as a 7-segment LED display, etc., is used for reducing cost.

Figure 5:
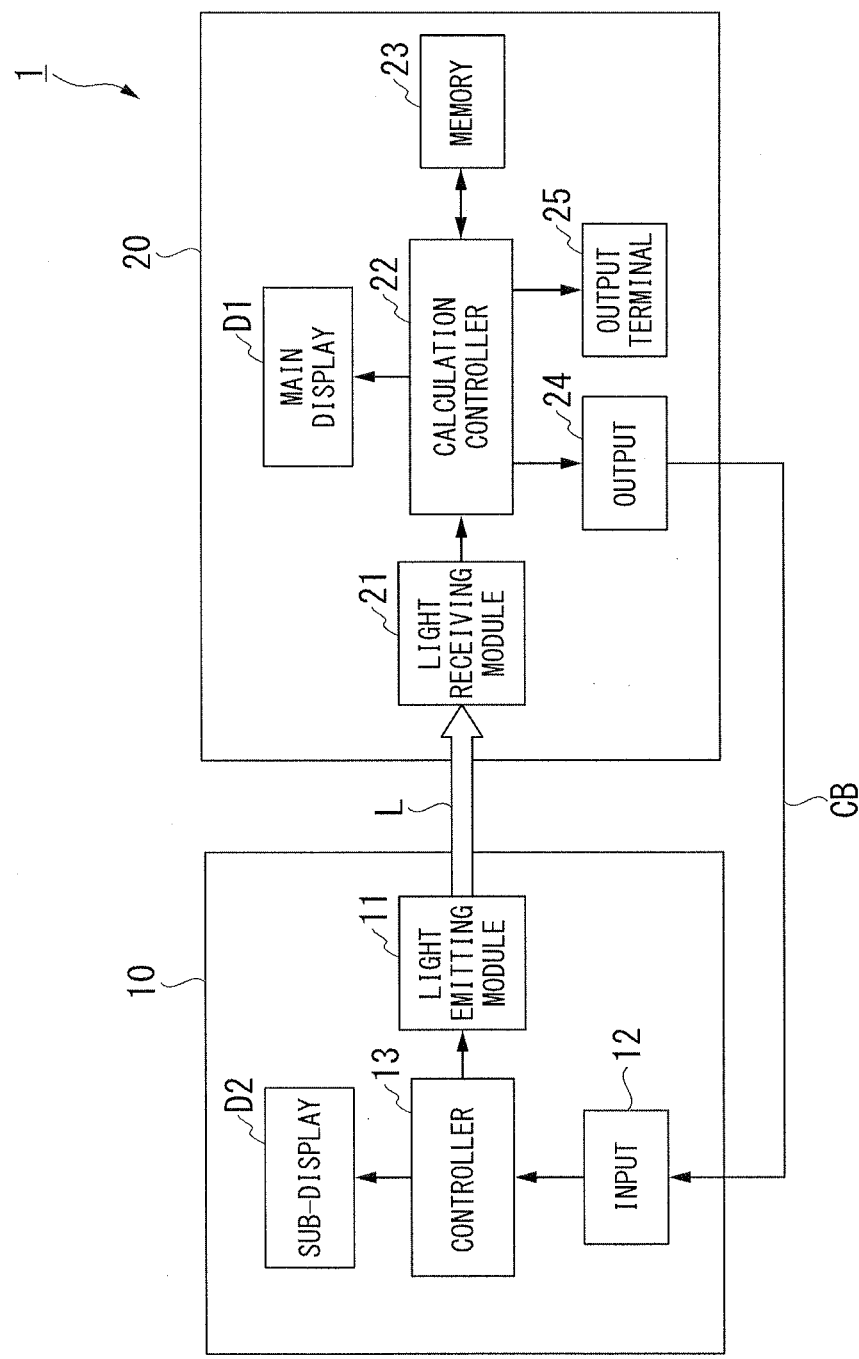
FIG. 5 is a block diagram illustrating an electrical configuration of the laser gas analyzer according to one embodiment of the present invention.

FIG. 5 is a block diagram illustrating an electrical configuration of a laser gas analyzer according to one embodiment of the present invention. As shown in FIG. 5, the light emitter 10 of the laser gas analyzer 1 includes a light emitting module 11, an input 12, and a controller 13 in addition to the above-described sub-display D2. Moreover, the light receiver 20 of the laser gas analyzer 1 includes a light receiving module 21, a calculation controller 22 or a calculation device, a memory 23, an output 24, and an output terminal 25.

The light emitting module 11, which includes light emitting elements such as a semiconductor laser, etc., emits a laser light L to be irradiated onto a gas to be measured X that flows in the pipe P under the control of the controller 13. The wavelength of the laser light L which is emitted from the light emitting module 11 is set in accordance with the gas to be measured X. The input 12 is connected to the output 24 provided in the light receiver 20 via a cable CB and takes a transmittance signal or a signal which indicates the transmittance of the laser light L output from the output 24 to output the input transmittance signal to the controller 13.

The controller 13 controls the light emitting module 11 to cause the laser light L to be irradiated onto the gas to be measured X to be emitted. More specifically, based on the detected result of the current which flows in the light emitting element provided in the light emitting module 11 or the detected result of the laser light L which is emitted from the light emitting module 11, the controller 13 controls the light emitting module 11 such that the intensity of the laser light L is constant and performs a control such that a certain wavelength region is swept. Moreover, the controller 13 performs a drive control of a sub-display D2 based on a transmittance signal from the input 12 and causes the transmittance of the laser light L that is indicated by a transmittance signal to be displayed on the sub-display D2.

The light receiving module 21, which includes a light receiving element such as a photodiode, etc., receives a light receiving signal acquired by receiving the laser light L to output the acquired light receiving signal to the calculation controller 22. The calculation controller 22 uses the light receiving signal from the light receiving module 21 to determine the used absorption spectrum of the laser light L and, based on this absorption spectrum, measures the components contained in the gas to be measured X and the concentration thereof, the transmittance of the laser light L, the temperature of the gas to be measured X, etc. Moreover, the calculation controller 22 performs a drive control of the main display D1 and causes multiple measured results of the gas to be measured X or the components contained in the gas to be measured X and the concentration thereof, the transmittance of the laser light L, the temperature of the gas to be measured X, etc., to be displayed on the main display D1.

Moreover, the calculation controller 22 compares a threshold value stored in the memory 23 and the transmittance of the laser light L that is acquired using the light receiving signal from the light receiving module 21 and causes the measured result to be displayed on the main display D1 in different modes when the transmittance of the laser light L does not exceed the threshold and when the transmittance of the laser light L exceeds the threshold. For example, the whole display region of the main display D1 is set to be a normal display such that letters are displayed in white on a black background when the transmittance of the laser light L does not exceed the threshold, while a half of the display region of the main display D1, for example, the bottom half, is set to be a reverse display such that letters are displayed in black and white on a white background when the transmittance of the laser light L exceeds the threshold value. Such displays are made to make it possible for a worker which performs an optical axis adjustment of the light receiver 20 to easily grasp the degree of adjustment of the optical axis.

The calculation controller 22 causes the transmittance of the laser light L or a part of the measured results to be displayed also on the sub-display D2 in different modes when the transmittance of the laser light L does not exceed the threshold value and when the transmittance of the laser light L exceeds the threshold value. For example, the measured result is caused to be displayed on the sub-display D2 in a flashing display when the transmittance of the laser light L does not exceed the threshold value and the measured result is caused to be displayed on the sub-display D2 in a lighting display or a normal display when the transmittance of the laser light L exceeds the threshold value. Such displaying is carried out for the worker which performs the optical axis adjustment of the light emitter 10 to easily grasp the degree of adjustment of the optical axis.

In addition, the calculation controller 22 causes different signals to be output from the output terminal 25 when the transmittance of the laser light L exceeds the threshold and when the transmittance of the laser light L does not exceed the threshold. For example, a signal in an audible frequency band with relatively low frequencies is caused to be output from the output terminal 25 when the transmittance of the laser light L does not exceed the threshold and a signal in an audible frequency band with relatively high frequencies is caused to be output from the output terminal 25 when the transmittance of the laser light L exceeds the threshold. Such outputting can be carried out for the worker to grasp the degree of adjustment of the optical axis with an auditory sense when the output terminal 25 is connected to a speaker, for example.

The memory 23, which is a non-volatile memory such as a flash ROM or a read only memory, an EEPROM or an electrically erasable and programmable ROM, etc., stores therein the above-described threshold value used at the time of the optical axis adjustment. Here, an arbitrary value may be set for the threshold value. For example, when it suffices that a rough transmittance be determined by the threshold value, a value of approximately "50%" is set, for example, a value of approximately "90%" is set, for example, when it is necessary to check the high-accuracy optical axis adjustment by the threshold value. Moreover, a single value may be set for the threshold value, or multiple values may be set for the threshold value. When the multiple values are set, every time the respective threshold values are exceeded, it is desirable to vary displaying of the main display D1 and the sub-display D2, or vary the signal output from the output terminal 25.

The output 24, which is connected to the input 12 of the light emitter 10 via a cable CB, outputs a transmittance signal indicating the transmittance of the laser light L that is determined in the calculation controller 22. This transmittance signal, which is a digital signal, is transmitted to the light emitter 10 via the cable CB without being affected by noise. The output terminal 25, which is a terminal meeting the explosion-proof standards, for example, is provided for externally outputting or transmitting the measured results of the calculation controller 22. This output terminal 25 may also be used for outputting the above-described signal in the audible frequency band.

Here, the reason that the main display D1, which can display the multiple measured results, is provided in the light receiver 20 is to decrease the effect of noise as well as to improve the signal processing efficiency. In other words, the main display D1 is provided in the light receiver 20, in which the calculation controller 22 is provided, to thereby eliminate the need for calculating a signal onto which noise is superimposed as in the related art to improve the signal processing efficiency and, moreover, to decrease the effect of noise by ensuring that the noise is not superimposed onto the light receiving signal as much as possible.

Moreover, the reason that the sub-display D2 which displays a part of the measured results or the transmittance of the laser light L that is displayed on the main display D1 is provided in the light emitter 10 is to make it possible for the worker, by himself, to efficiently carry out the optical axis adjustment of the light emitter 10. The optical axis adjustment of the laser gas analyzer 1 is governed by the optical axis adjustment of the light emitter 10. In other words, unless the optical axis adjustment of the light emitter 10 is carried out to some extent, the optical axis adjustment of the light receiver 20 becomes meaningless. In this way, in order for the optical axis adjustment of the light emitter 10 that is to be governing to be efficiently carried out by himself, the sub-display D2 is provided in the light receiver 10.

Figure 6:
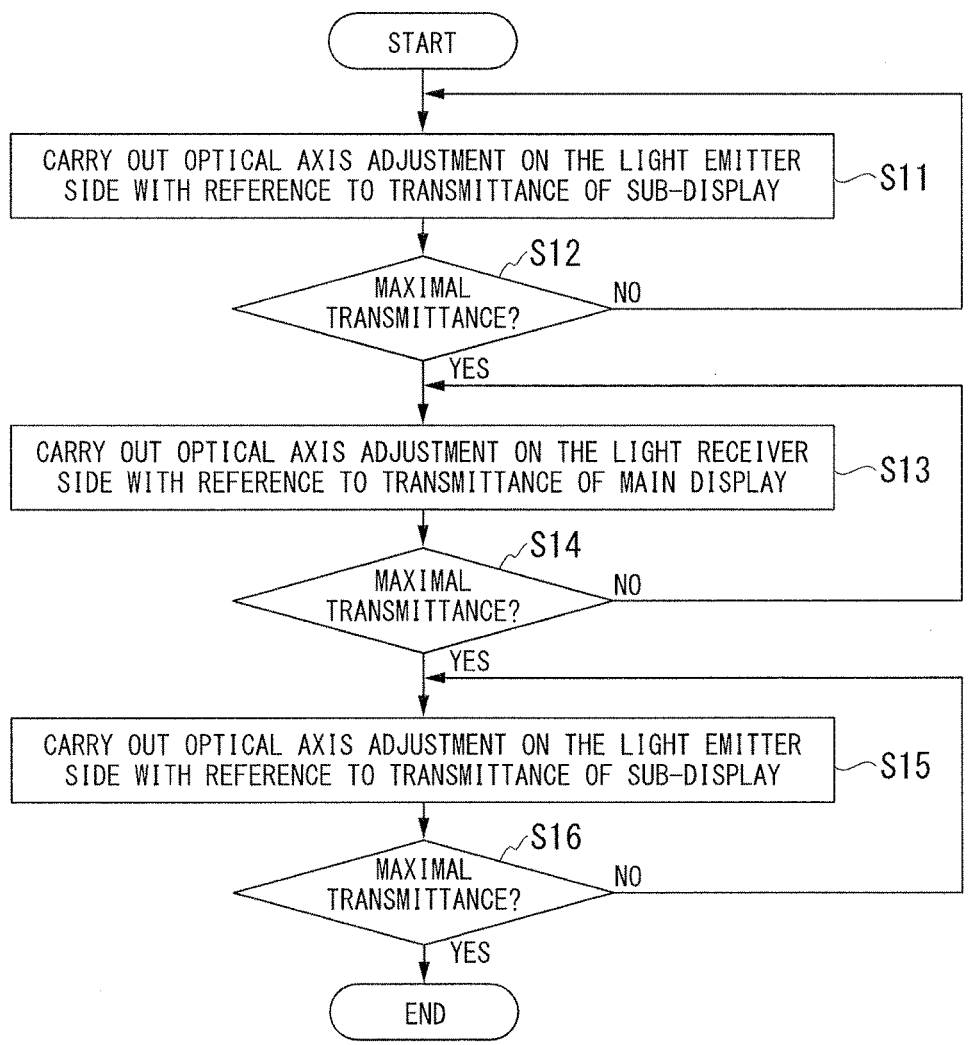
FIG. 6 is a flowchart illustrating an optical axis adjustment procedure of a laser gas analyzer 1 according to one embodiment of the present invention.

A method is described of adjusting an optical axis of the laser gas analyzer 1 in the above-described configuration. FIG. 6 is a flowchart illustrating an optical-axis adjustment procedure of the laser gas analyzer 1 according to one embodiment of the present invention. The optical axis adjustment of the laser gas analyzer 1 is carried out by one worker at the time of installing the laser gas analyzer 1 or at the time of periodic or aperiodic maintenance of the laser gas analyzer 1.

When a task is started, first the worker visits the installed position of the light emitter 10 to carry out a task of adjusting the optical axis of the light emitter 10 with reference to the transmittance of the laser light L displayed in the sub-display D2 (procedure S11). More specifically, a task of adjusting the adjusting screws N (see FIG. 2) of the optical axis adjustment mechanism provided in the light emitter 10 is carried out such that the transmittance of the laser light L is maximal while checking the display content or the transmittance of the laser light L of the main display D1 shown in FIG. 3. While this task is being carried out, whether the transmittance of the laser light L reached the maximum is determined by the worker (procedure S12). If it is determined by the worker that the transmittance of the laser L is not maximal or when the determined result of procedure S11 is "NO", the task of adjusting the optical axis of the light emitter 10 is continued (procedure S11).

On the other hand, if it is determined by the worker that the transmittance of the laser light L is maximal or when the determined result of procedure S12 is "YES", the worker visits the installed position of the light receiver 20 and carries out the task of adjusting the optical axis of the light receiver 20 with reference to the transmittance of the laser light L that is displayed on the main display D1 (procedure S13). More specifically, a task of adjusting the adjusting screws N of the optical axis adjustment mechanism provided in the light receiver 20 is carried out such that the transmittance of the laser light L is maximal while checking the transmittance of the laser light L of the display content of the sub-display D2 shown in FIG. 4.

While this task is carried out, whether the transmittance of the laser light L is maximal is determined by the worker (procedure S14). If it is determined by the worker that the transmittance of the laser light L is not maximal or when the determined result of the procedure S14 is "NO", the task of adjusting the optical axis of the light receiver 20 is continued (procedure S13).

On the other hand, if it is determined by the worker that the transmittance of the laser light is maximal or when the determined result of the procedure S14 is "YES", the worker again visits the installed position of the light emitter 10 to carry out a task of adjusting the optical axis of the light emitter 10 with reference to the transmittance of the laser light L displayed in the sub-display D2 (procedure S15). While this task is being carried out, whether the transmittance of the laser light L is maximal is determined by the worker (procedure S16). If it is determined by the worker that the transmittance of the laser light L is not maximal or when the determined result of procedure S16 is "YES", a series of tasks shown in FIG. 6 is completed.

As described above, according to the present embodiment, the main display D1 which displays the measured result acquired by receiving the laser light L which transmitted the gas to be measured X is provided in the light receiver 20 of the laser gas analyzer 1 and the sub-display D2 which displays a part of measured results displayed on the main display D1 is provided in the light emitter 10 of the laser gas analyzer 1. Therefore, the worker may efficiently carry out, by himself, the optical axis adjustment of the light emitter 10 with reference to the display content of the sub-display D2 provided in the light emitter 10 and also efficiently carry out, by himself, the optical axis adjustment with reference to the display content of the main display D1 provided in the light receiver 20.

Here, in the calculation controller 22 of the laser gas analyzer 1, to improve the S/N or signal-to-noise ratio, a process is carried out to average the absorption spectrum of the laser light L over a certain time period or approximately several seconds to several tens of seconds, for example, and components contained in the gas to be measured X and the concentration thereof, etc., are measured based on the averaged absorption spectrum. Thus, the display content of the main display D1 and the sub-display D2 is updated for each of the above-described certain time periods or calculation periods of the calculation controller 22. The calculation period of the calculation controller 22 varies depending on the gas to be measured X and the measurement environment, so that the period over which the display content of the main display D1 and the sub-display D2 is updated, or update period also varies.

When the measured result or the transmittance, for example, displayed on the main display D1 or the sub-display D2 varies, the fact that the update period has arrived may be known; however, the fact that the update period has arrived may not be known unless the measured result changes. For example, while carrying out fine adjustment of the optical axis or carrying out a final check as to whether the optical-axis adjustment has been completed to result in a stable transmittance, it is often the case that the measured result which is displayed on the main display D1 or the sub-display D2 often does not change. Therefore, the above-described update period may be reported to the worker.

Figure 7A:
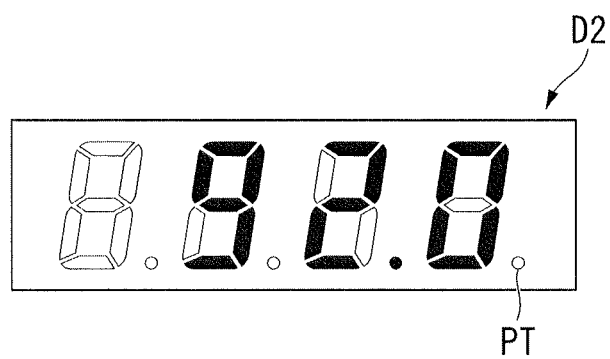
FIGS. 7A and 7B are diagrams illustrating an exemplary report of an update period in the sub-display according to one embodiment of the present invention.
Figure 7B:
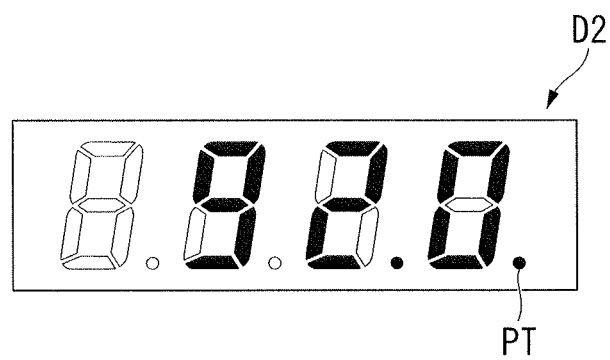

FIGS. 7A and 7B are diagrams illustrating exemplary reports of an update period in the sub-display according to one embodiment of the present invention. The sub-display D2 shown in FIGS. 7A and 7B, which is the same as the sub-display D2 shown in FIG. 4, is a 7-segment LED display, for example. In an example shown in FIGS. 7A and 7B, the transmittance "92.0" of the laser light is displayed. In the sub-display D2 on which such transmittance of the laser light is displayed, the rightmost decimal point PT1 is not used. Therefore, based on a signal from the calculation controller 22, for example, alternately carrying out, for each update period, displaying or toggle displaying between displaying which causes the decimal point PT to be turned on (see FIG. 7A) and displaying which causes the decimal point PT to be turned off (see FIG. 7B) makes it possible to report the update period to the worker without involving an increased cost.

Figure 8A:
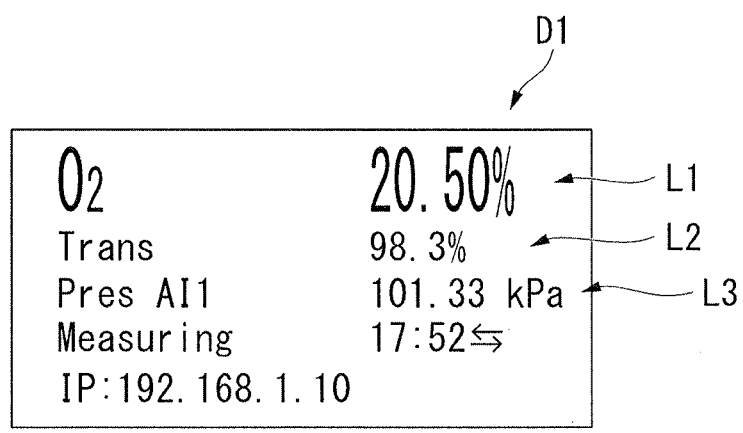
FIGS. 8A and 8B are diagrams illustrating one exemplary report of an update period in the main display according to one embodiment of the present invention.
Figure 8B:
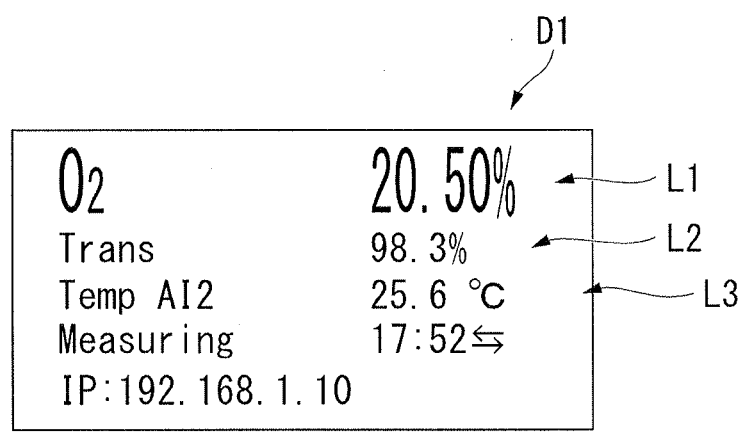

FIGS. 8A and 8B are diagrams illustrating exemplary reports of an update period in the main display according to one embodiment of the present invention. The main display D1 which is shown in FIGS. 8A and 8B, which is the same as the main display D1 shown in FIG. 3, is a liquid crystal display, for example. In an example shown in FIGS. 8A and 8B, "20.50%" is displayed as the concentration "$O_2$" of the gas to be measured X and "98.3%" is displayed as the transmittance "Trans" of the laser light. Moreover, "17:52" is displayed as the measured time "Measuring" and "IP: 192.168.1.10" is displayed as an IP address of the laser gas analyzer 1. Moreover, in an example shown in FIG. 8A, "101.33 kPa" is displayed as a measured result of pressure "PresAI1" on a third line L3 or a line which follows a first line L1 on which the concentration "$O_2$" of the gas to be measured X is displayed and a second line L2 on which the transmittance "Trans" of the laser light is displayed, while in an example shown in FIG. 8B, "25.6° C." is displayed as the measured temperature result "Temp AI2" on the third line L3.

In the main display D1 on which the above-described displaying may be made, multiple measured results, etc., are displayed in addition to the transmittance "Trans" of the laser light. Therefore, alternate displaying or toggle displaying of measured results other than the transmittance "Trans"

of the laser light may be made for each update period to report the update period to the worker without involving an increased cost. For example, alternate switching is made for each update period between displaying of a third line L3 shown in FIG. 7A or displaying indicating the measured pressure result "Pres AI1" and displaying of a third line L3 shown in FIG. 7B or displaying indicating the measured temperature result "Temp AI2". Such displaying may be made for the worker to know the update period from the change in displaying on the third line L3 even when a value of the concentration on the first line L1 and a value of the transmittance on the second line L2 do not change.

Figure 9:
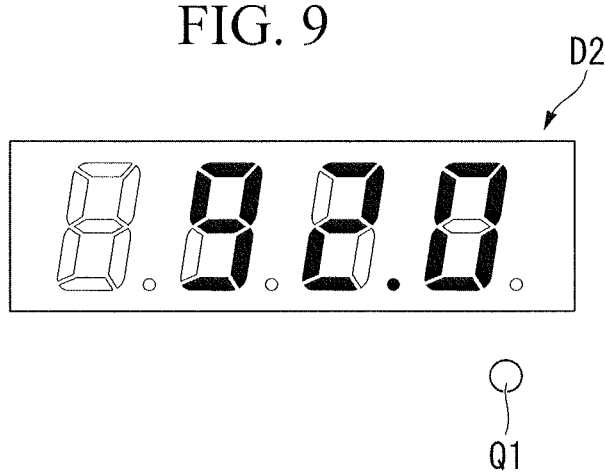
FIG. 9 is a diagram illustrating another exemplary report of the update period in the sub-display according to one embodiment of the present invention.

FIG. 9 is a diagram illustrating another exemplary report of an update period in the sub-display according to one embodiment of the present invention. In an example in FIG. 9, with a light-emitting element Q1 such as an LED element, etc., being provided in the vicinity of the sub-display D2, an operation or toggle lighting is carried out such that turning on of the light emitting element Q1 and turning off of the light emitting element Q1 are alternately performed for each update period based on a signal from the calculation controller 22. In the example shown in FIG. 9, while there is a need to provide the light emitting element Q1, the update period may be reported to the worker without involving a significant increase in cost.

Figure 10:
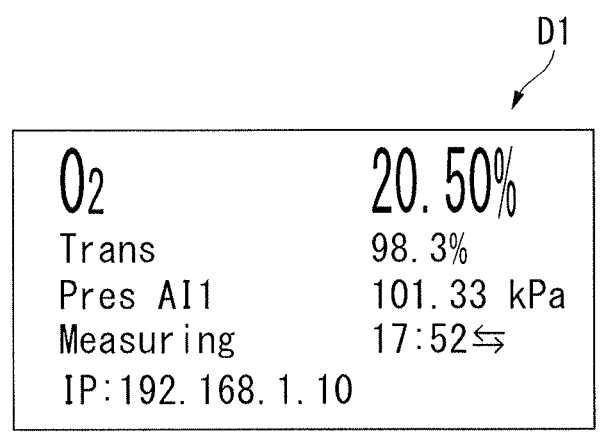
FIG. 10 is a diagram illustrating a further exemplary report of the update period in the main display according to one embodiment of the present invention.
Figure 10:
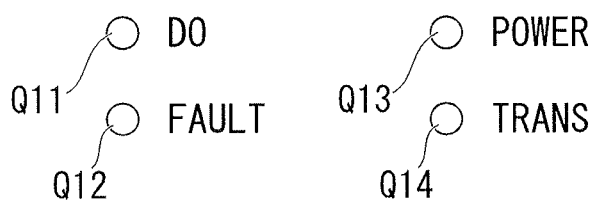

FIG. 10 is a diagram illustrating a further exemplary report of an update period in the main display according to one embodiment of the present invention. In an example shown in FIG. 10, with a light emitting element Q14 being provided for light emitting elements Q11-Q13 provided in the vicinity of the main display D1, an operation or toggle lighting is carried out such that turning on of the light emitting element Q14 and turning off of the light emitting element Q14 are alternately performed for each update period based on a signal from the calculation controller 22 in the same manner as the example shown in FIG. 9. The light-emitting elements Q11-Q13, which are provided in the vicinity of the main display D1 is a light-emitting element such as an LED, etc., provided to indicate the states of the laser gas analyzer 1. For example, the light emitting element Q11 is an orange-colored light emitting element which indicates an alarm (DO), the light emitting element Q12 is a red-colored light emitting element which indicates a fault (FAULT), and the light emitting element Q13 is a green-colored light emitting element which indicates turning on the power (POWER). While the light emitting element Q14 needs to be provided in an example shown in FIG. 10 in the same manner as FIG. 9, the update period may be reported to the worker without involving a substantial cost increase.

The update period may be reported to the worker in methods explained using FIGS. 7-10 for the worker to accurately carry out tasks by checking the update period reported without the need to grasp update periods which vary for the respective laser gas analyzer 1. In this way, the task efficiency and the accuracy of the optical-axis adjustment in the laser gas analyzer 1 may be improved.

While a display according to one embodiment of the present invention has been described in the foregoing, the present invention is not restricted to the above-described embodiments, and changes can be made freely within the scope of the present invention. For example, while the display content of the main display D1 and of the sub-display 2 is varied depending on whether the transmittance of the laser light L exceeded a threshold value stored in the memory 23 in the above-described embodiment, how the transmittance of the laser light L is changed may be analyzed to display a direction in which the optical axis is adjusted with an arrow.

Moreover, in the above-described embodiment, an example is described of performing an optical-axis adjustment of the light emitter 10 with reference to the display content of the sub-display D2 and performing an optical-axis adjustment of the light receiver 20 based on the display content of the main display D1. However, a speaker may be connected to the output terminal 25 shown in FIG. 5 and a sound emitted from the speaker may be referred to in order to perform optical-axis adjustment of the light emitter 10 and the light receiver 20. Moreover, a signal which indicates a calculation period or update period of the calculation controller 22 may be caused to be output from the output terminal 25 and the update period may be reported with the sound emitted from the speaker.

Furthermore, in the above-described embodiment, a configuration is described such that the calculation controller 22 and the main display D1 are provided in the light receiver 20 and the sub-display D2 is provided in the light receiver 10. However, conversely thereto, the calculation controller 22 and the main display D1 may be provided in the light emitter 10, and the sub-display D2 may be provided in the light receiver 20. With this configuration, a light receiving signal which is acquired in the light receiving module 21 of the light receiver 20 needs to be conveyed to the light emitter 10, resulting in the need for preventing noise from mixing into the light receiving signal.

Moreover, in the above-described embodiment, an example is described of performing toggle displaying on the main display D1 and the sub-display D2 (see FIGS. 7 and 8) and performing toggle lighting of the light emitting elements Q1 and Q14. However, the mode of displaying on the main display D1 and the sub-display D2 and the mode of light emitting of the light emitting elements Q1 and Q14 are arbitrary. For example, the mode of displaying may be performed such that, on the main display D1 and the sub-display D2, the transmittance display is displayed only instantaneously at an instance at which the update period arrived, after which re-displaying is made.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:
1. A laser gas analyzer, comprising:
a light emitter having a laser light emitting element which emits a laser light irradiated onto a gas to be measured;
a light receiver having a light receiving element which receives a laser light which transmitted the gas to be measured;
a plurality of optical-axis adjustment mechanisms, one of which is provided in the light emitter and the other one of which is provided in the light receiver;
a calculation device which is provided in one of the light emitter and the light receiver and which calculates a measured result using a light receiving signal which is acquired by receiving the laser light which transmitted the gas to be measured, a main display which is provided in one of the light emitter and the light receiver and displays thereon the measured result; and a sub-display which is provided in the other one of the light emitter and the light receiver and displays thereon a part of the measured result displayed on the main display, wherein at least one of the main display and sub-display varies at least a part of the display content for each calculation period of the calculation device.

2. The laser gas analyzer as claimed in claim 1, wherein the main display displays thereon at least information which indicates a concentration of the gas to be measured and a transmittance of the laser light, and the sub-display displays information indicating the transmittance of the laser light as a part of the measured result.

3. The laser gas analyzer as claimed in claim 1, wherein the main display and the calculation device are provided in the light receiver, and the sub-display is provided in the light emitter.

4. The laser gas analyzer as claimed in claim 1, further comprising a memory which stores therein a threshold value for a transmittance of the laser light, wherein the main display and the sub-display display the measured result and the part of the measured result in modes which are different when the transmittance of the laser light does not exceed the threshold value and when the transmittance of the laser light exceeds the threshold value.

5. The laser gas analyzer as claimed in claim 4, further comprising an output terminal which externally outputs signals which are different when the transmittance of the laser light does not exceed the threshold value and when the transmittance of the laser light exceeds the threshold value.

6. The laser gas analyzer as claimed in claim 1, wherein a light emitting element which emits light for each calculation period of the calculation device is included in at least one of the light emitter and the light receiver.

7. A laser gas analyzer, comprising:

a light emitter having a laser light emitting element which emits a laser light irradiated onto a gas to be measured;

a light receiver having a laser light receiving element which receives a laser light which transmitted the gas to be measured;

a plurality of optical-axis adjustment mechanisms, one of which is provided in the light emitter and the other one of which is provided in the light receiver;

a main display which is provided in the light receiver and which displays thereon the measured result acquired by receiving the laser light which transmitted the gas to be measured;

a sub-display which is provided in the light emitter and displays thereon a part of the measured result displayed on the main display;

a calculation device which is provided in the light receiver and which performs a calculation on the measured result using a light receiving signal which is acquired by receiving the laser light which transmitted the gas to be measured, the calculated measured result including a transmittance of the laser light; and a memory which stores therein a threshold value for the transmittance of the laser light, wherein the calculation device compares the stored threshold value in the memory and the transmittance of the laser light that is acquired using the light receiving signal, determines whether the transmittance of the laser light exceeds the stored threshold value, and causes the measured result to be displayed on the main display in a first mode when the transmittance of the laser light does not exceed the stored threshold value and causes the measured result to be displayed on the main display in a second mode when the transmittance of the laser light exceeds the stored threshold value and the first mode and the second mode are different from each other.

8. The laser gas analyzer as claimed in claim 7, wherein the calculation device further causes the measured result to be displayed on the sub-display in a third mode when the transmittance of the laser light does not exceed the stored threshold value and causes the measured result to be displayed on the sub-display in a fourth mode when the transmittance of the laser light exceeds the stored threshold value and the third mode and the fourth mode are different from each other.

9. The laser gas analyzer as claimed in claim 1, wherein at least one of the main display and sub-display alternately varies at least a part of the display content other than an area where information indicating transmittance of the laser light is displayed, for each calculation period of the calculation device.

* * * * *